(12) United States Patent
Chuang

(10) Patent No.: US 7,847,140 B2
(45) Date of Patent: Dec. 7, 2010

(54) PROCESS FOR MAKING HIGHER OLEFINS

(76) Inventor: Karl Chuang, 624 Harker Close, Edmonton, Alberta (CA) T6R 2X7

( * ) Notice: Subject to any disclaimer, the term of this patent is extended or adjusted under 35 U.S.C. 154(b) by 348 days.

(21) Appl. No.: 12/068,905

(22) Filed: Feb. 13, 2008

(65) Prior Publication Data

US 2009/0203946 A1 Aug. 13, 2009

(51) Int. Cl.
*C07C 2/02* (2006.01)
(52) U.S. Cl. .................. 585/531; 585/510; 585/515; 585/520; 585/526; 585/530; 203/29; 203/38; 203/DIG. 6
(58) Field of Classification Search ............... 585/510, 585/511, 515, 520, 530, 531; 203/29, 38, 203/DIG. 6
See application file for complete search history.

(56) References Cited

U.S. PATENT DOCUMENTS 6,004,256 A * 12/1999 Townsend et al. .......... 585/517
7,259,285 B1 * 8/2007 Walter et al. ............... 585/513
2006/0036049 A1 * 2/2006 Zhao et al. ................. 526/172

FOREIGN PATENT DOCUMENTS

WO WO 2005056503 A1 * 6/2005

OTHER PUBLICATIONS

Zhang, et. al., "Oligomerization of Ethylene in a Slurry Reactor using a Nickel/Sulfated Alumina Catalyst", Ind. Eng. Chem. Res., 1997, 36, 3433-3438.*
Sundaram, et. al., "Ethylene" in Kirk-Othmer Encyclopedia of Chemical Technology, John Wiley, 2001, available on-line Apr. 16, 2001.*
NIST Data (NIST Web-book, Standard Reference Data, available on-line at webbook.nist.gov).*

* cited by examiner

*Primary Examiner*—Glenn A Caldarola
*Assistant Examiner*—Bradley Etherton
(74) *Attorney, Agent, or Firm*—George A. Seaby

(57) ABSTRACT

A process is disclosed for making higher olefins by oligomerization of a lower olefin e.g ethylene, to higher olefins, using catalytic distillation conditions. Simultaneously and interdependently, the lower olefin is catalytically oligomerized to higher olefins, and said higher olefins are separated and recovered as liquid.

10 Claims, 7 Drawing Sheets

PROCESS FOR MAKING HIGHER OLEFINS

FIELD OF THE INVENTION

The present invention relates to manufacture of higher olefins by oligomerization of a lower olefin, and in particular to oligomerization of ethylene, with simultaneous separation of the higher olefins, using catalytic distillation conditions. The process is operated without the need for added solvent, in contrast to the prior art.

BACKGROUND OF THE INVENTION

Several catalytic processes have been developed for oligomerization of olefins to higher olefins, and in particular for oligomerization of ethylene to a series of higher olefins $(C_2H_4)_n$ (Equation 1).

$$C_2H_4 <==> C_4H_8, C_6H_{12}, C_8H_{16},\qquad(1)$$

i. [Catalyst]

The higher olefins initially so formed normally are terminal(alpha) olefins ie. olefins having a single double bond at the first carbon atom. The terminal olefins may then isomerize to one or more internal olefins ie olefins having a double bond on an interior carbon atom. However, usually the terminal olefins have higher commercial utility and value than the internal olefins. For example, it is desirable to use terminal olefins in combination with ethylene to form partially branched polyolefin co-monomers, biodegradable detergents, lubricants, or plasticizers.

Thus it is desirable to operate the catalytic reaction of the process under conditions where the isomerisation reaction is minimized, thus ensuring a higher selectivity to terminal olefins. Operation at low temperatures minimizes the rate of the isomerisation reaction. However, it also is desirable to have a high reaction rate. Operation of the process at high temperatures provides a higher reaction rate than low temperatures. However, this requires high reactor pressures to allow for high olefin concentrations in the liquid phase.

There are at present three major commercial processes in use for oligomerization of olefins, each of which has a relatively high degree of complexity and less than a desirable efficiency. Both Chevron and Ethyl Corporation use Ziegler type catalysts in a homogeneous catalyst system. The Shell Higher Olefins Process (SHOP) uses a complex of nickel as the catalyst. Each of these systems uses a solvent and a catalyst in a liquid-phase reactor necessarily equipped with an intercooler. The mixture in the product stream is then purified in a series of separation columns.

Solid state catalyst processes used in slurry reactor systems allow for easier separation of the catalyst from the reaction mixtures but present several challenges. There is strong adsorption of the products on the catalyst surfaces, as well as on the reactant. Also, there is a negative thermodynamic influence on selectivity to the desired terminal olefin products at high reaction temperatures, with internal olefins being formed. There is a need for more active catalysts. Each of these factors including catalyst deactivation by the formation of decomposition and isomerisation products, must be overcome.

There are several bases for potential beneficial changes that would improve oligomerization processes, including use of milder conditions, thereby maximizing selectivity, and development of more active and selective catalysts, thereby enhancing yield and production rate.

Among the many catalysts known to catalyze the oligomerization of olefins, it has been found that highly acidic heterogeneous catalysts comprising, for example, finely divided nickel supported on sulfated alumina are particularly active for dimerization of propylene, as described in French Patent 2641 477 issued in 1990. The Ni/sulphated $Al_2O_3$ catalyst used in '477 is active at room temperature for dimerization of propylene in a slurry with an inert hydrocarbon solvent. Further, a similar catalyst comprising Ni/sulfonated non-porous $Al_2O_3$ (commercially available ALON) was shown to be active for oligomerization of ethylene, as described by Zhang et al. in "Oligomerization of Ethylene in a Slurry Reactor Using a Nickel/Sulfonated Alumina Catalyst," Ind. Eng. Chem. Res., 36, 3433-3438 (1997), the disclosure of which is incorporated herein by reference.

Several additional processes for oligomerization of olefins have been described in patents and the open literature. Among these are descriptions of catalyst systems for oligomerization of ethylene using either homogeneous or heterogeneous catalysts. However, a characteristic of all prior art is the use of a solvent that is necessary for conducting the process, in contrast to the process of the present invention. Examples of other prior art from which the present invention is so distinguished include: Krug et al. in U.S. Pat. No. 6,841,711; Gildert et al. in U.S. Pat. 6,274,783, Vora et al. in U.S. Pat. No. 6,025,53 and Townsend et al. in U.S. Pat. No. 6,004,256.

SUMMARY OF THE INVENTION

It is an object of the present invention to provide a process for oligomerization of lower olefins, and in particular for oligomerization of ethylene, without use of an added solvent, so that there is no need for separation of the higher olefins product from a fluid such as a hydrocarbon solvent. The process operates under catalytic distillation conditions such that the product higher olefins are in liquid form, so that the product is easily separated from the reaction mixture as liquid.

According to the invention, a process is provided for making higher olefins of formula $C_nH_{2n}$, wherein n is an integer greater than two through catalytic oligomerization of lower olefins wherein n is an integer from 2 to 5, and in particular to oligomerization of ethylene, and simultaneous separation of the higher olefins as liquid using catalytic distillation conditions e.g. in a catalytic distillation column. There is no need for added solvent. The process, which can be continuous, is operated at a temperature and a pressure such that the higher olefins are primarily in the liquid phase and the ethylene is present both as gas and dissolved phase, to form a solution with the liquid higher olefins. Suitable catalysts include the homogeneous and heterogeneous catalysts described above e.g. a catalyst comprising nickel dispersed on a non-porous alumina support is highly active and has good selectivity to terminal olefins at low temperatures. For example, the above-described catalyst known as ALON has been found to be useful If the catalyst is solid, it is called heterogeneous (gas-solid or liquid solid). If the solid or liquid catalyst is dissolved in the liquid reaction mixture, there is only one phase (liquid), thus called homogeneous catalyst.

BRIEF DESCRIPTION OF THE DRAWINGS

For a more complete understanding of the present invention and for further objects and advantages thereof, reference is made to the following description taken in conjunction with the accompanying drawings.

DETAILED DESCRIPTION OF THE INVENTION

The following description comprises data obtained through laboratory experiments and simulations using ASPEN PLUS.

Figure 1:
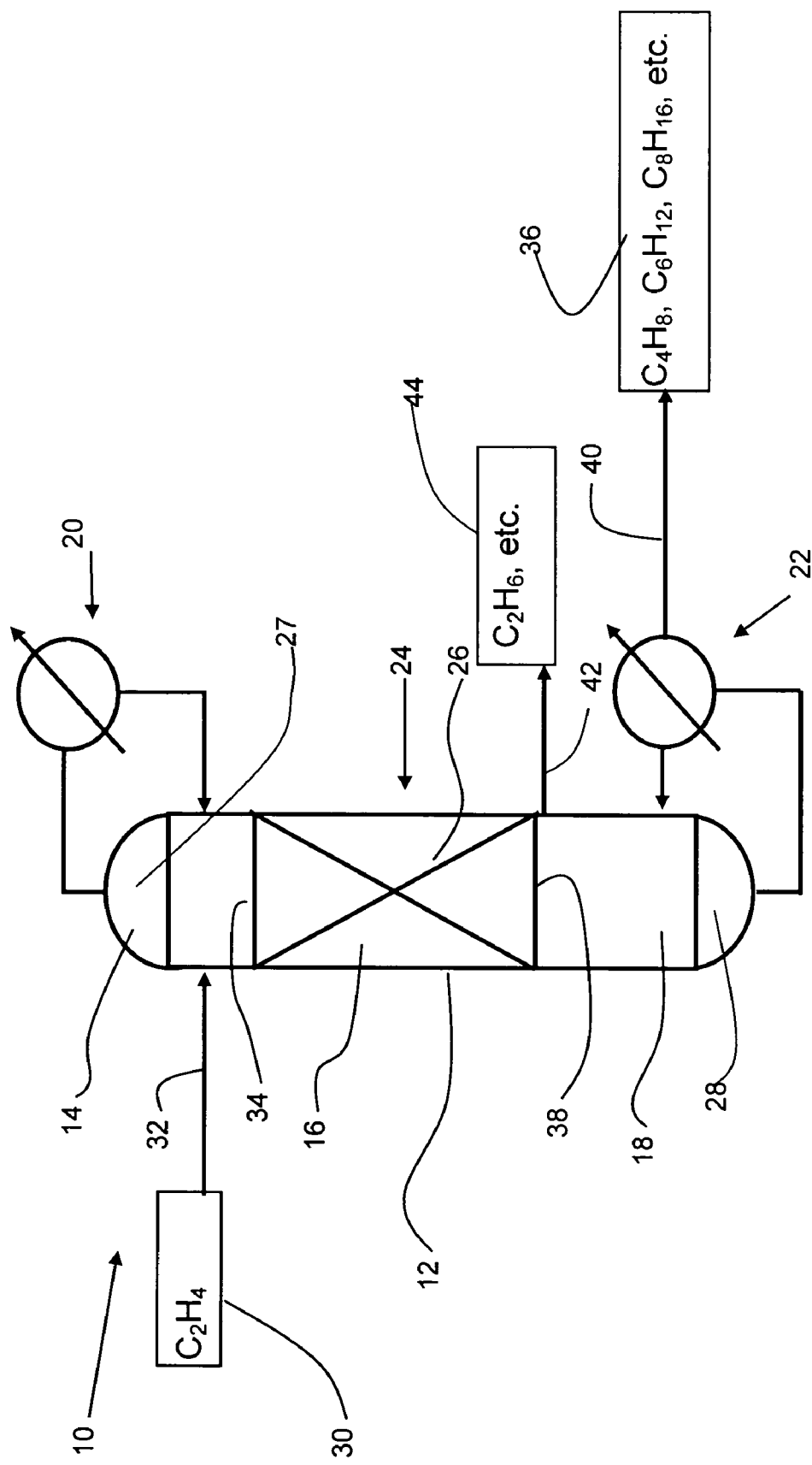
FIG. 1 is a schematic diagram of a catalytic distillation for concurrent oligomerization of ethylene and separation of higher olefins.
Figure 2:
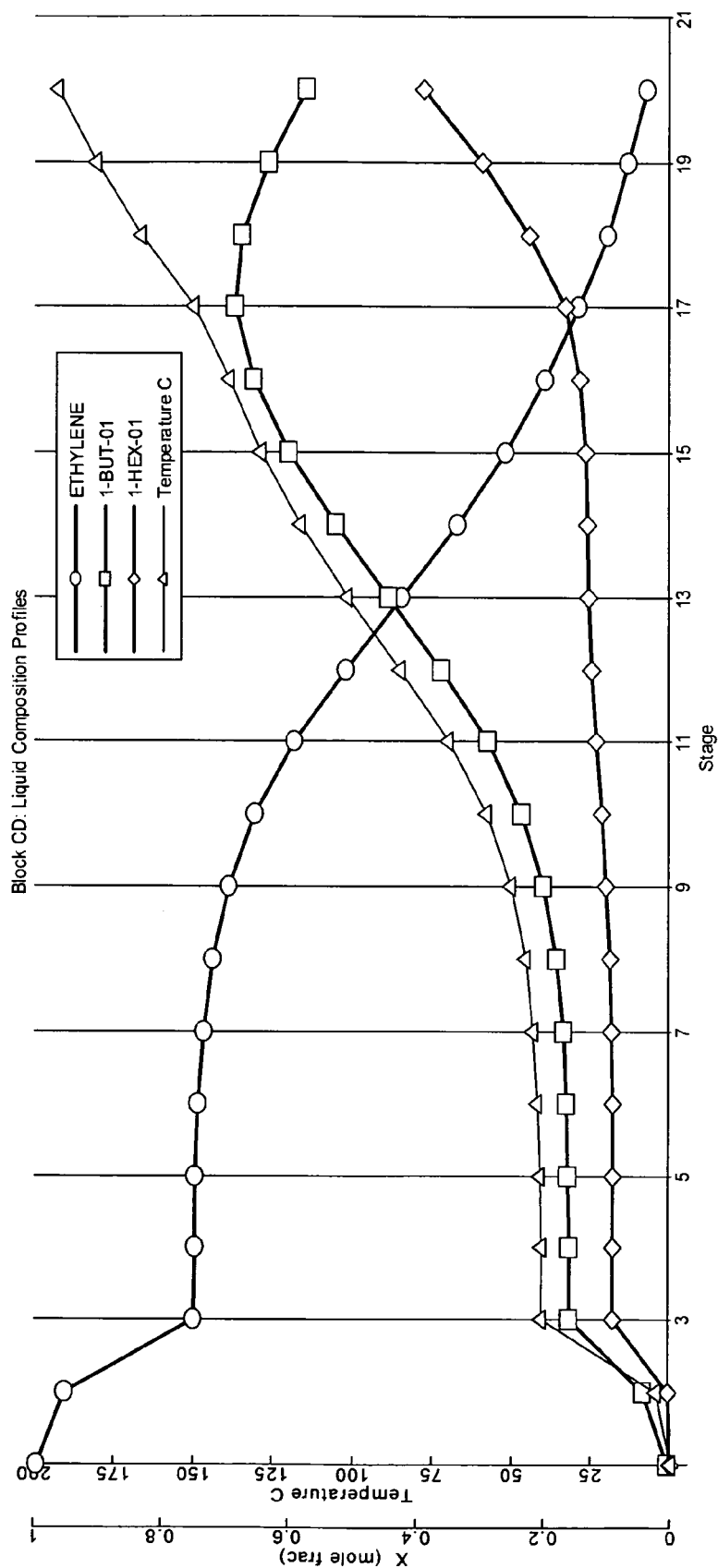
FIG. 2 shows a first profile of composition and temperature from modeling of the process of ethylene oligomerization using a catalytic distillation column. P=40 atm, RR=12, D/F=0.45, RXN at Stage 3, Equilibrium conversion=0.05, Total conversion of Ethylene=54.36%. Stage 1 is at the top of the column.
Figure 3:
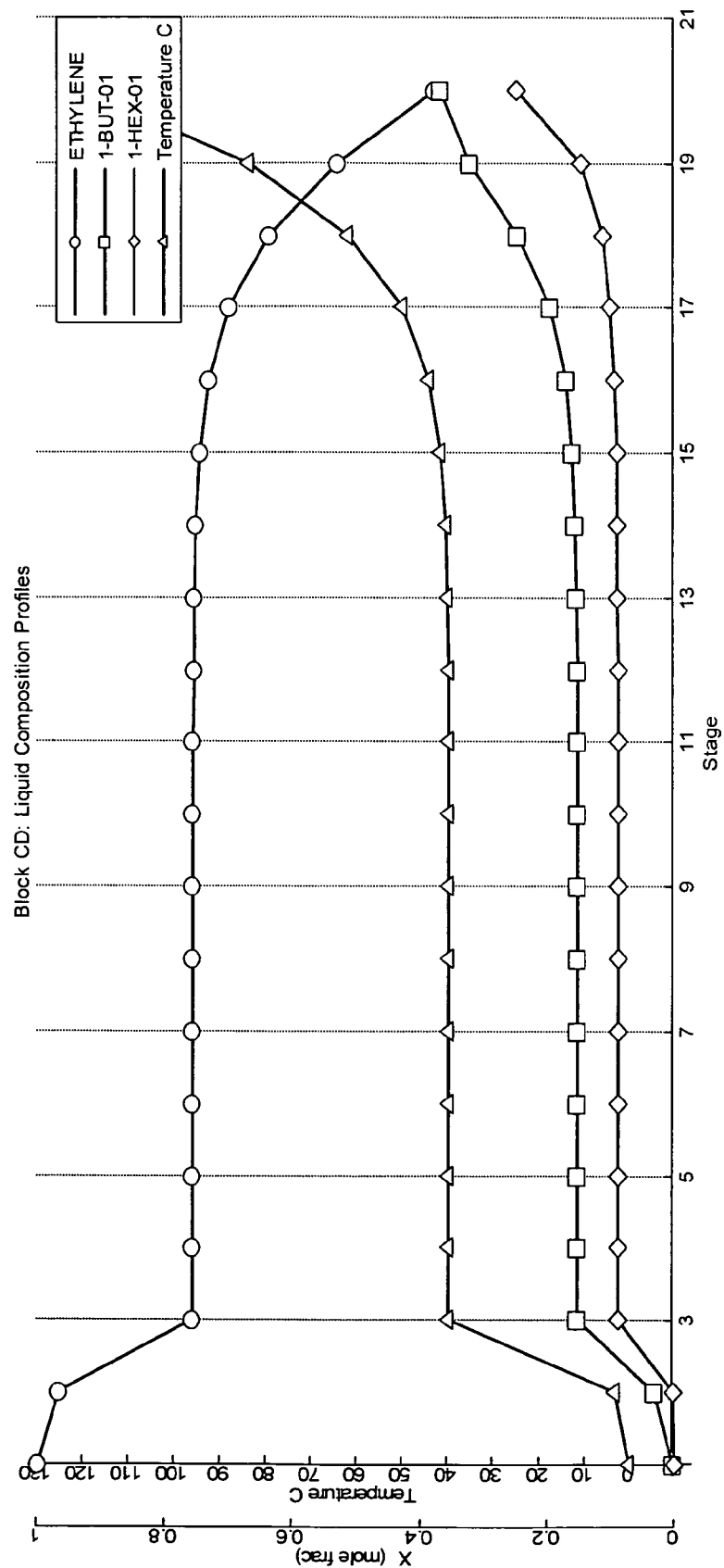
FIG. 3 shows a second profile of composition and temperature from modeling of the process of ethylene oligomerization using a catalytic distillation column. P=40 atm, RR=12, D/F=0.45, RXN at Stage 3, Equilibrium conversion=0.05, Total conversion of Ethylene=44.03%.
Figure 4:
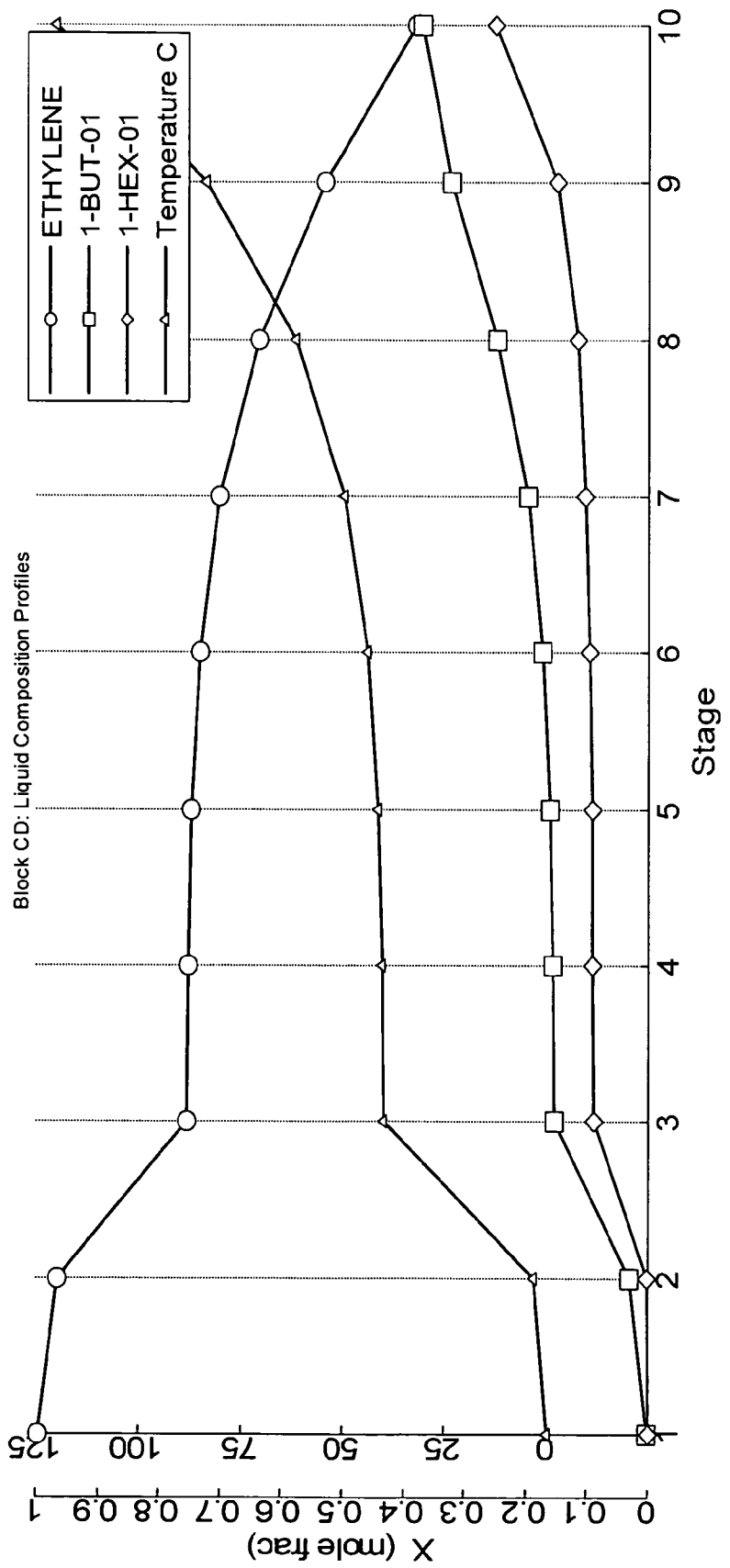
FIG. 4 shows a third profile of composition and temperature from modeling of the process of ethylene oligomerization using a catalytic distillation column. P=40 atm, RR=12, D/F=0.45, RXN at Stage 3, Equilibrium conversion=0.05, Total conversion of Ethylene=44.03%.
Figure 5:
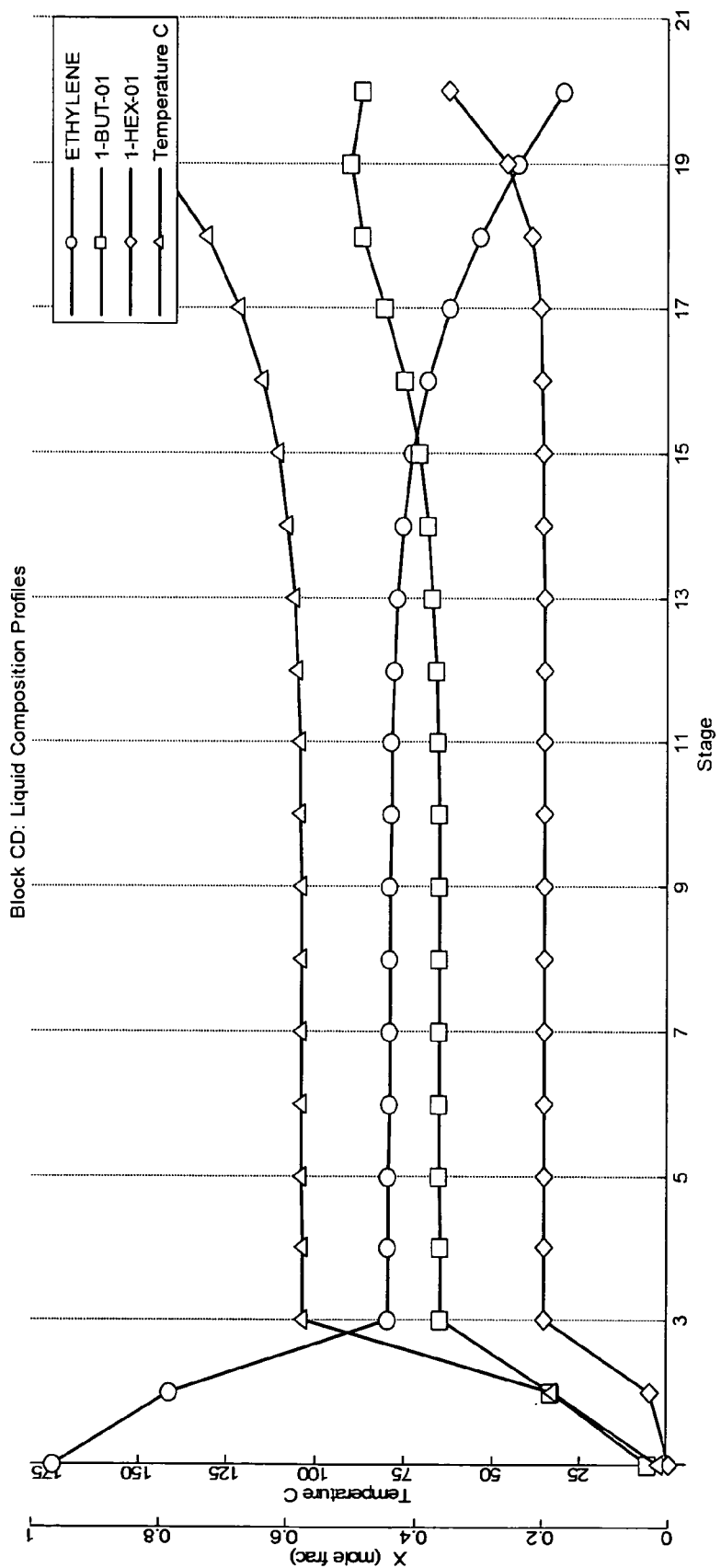
FIG. 5 shows a fourth profile of composition and temperature from modeling of the process of ethylene oligomerization using a catalytic distillation column. P=40 atm, RR=15, D/F=0.35, RXN=Stage 3, Equilibrium conversion=0.10, Total conversion of Ethylene=61.27%.
Figure 6:
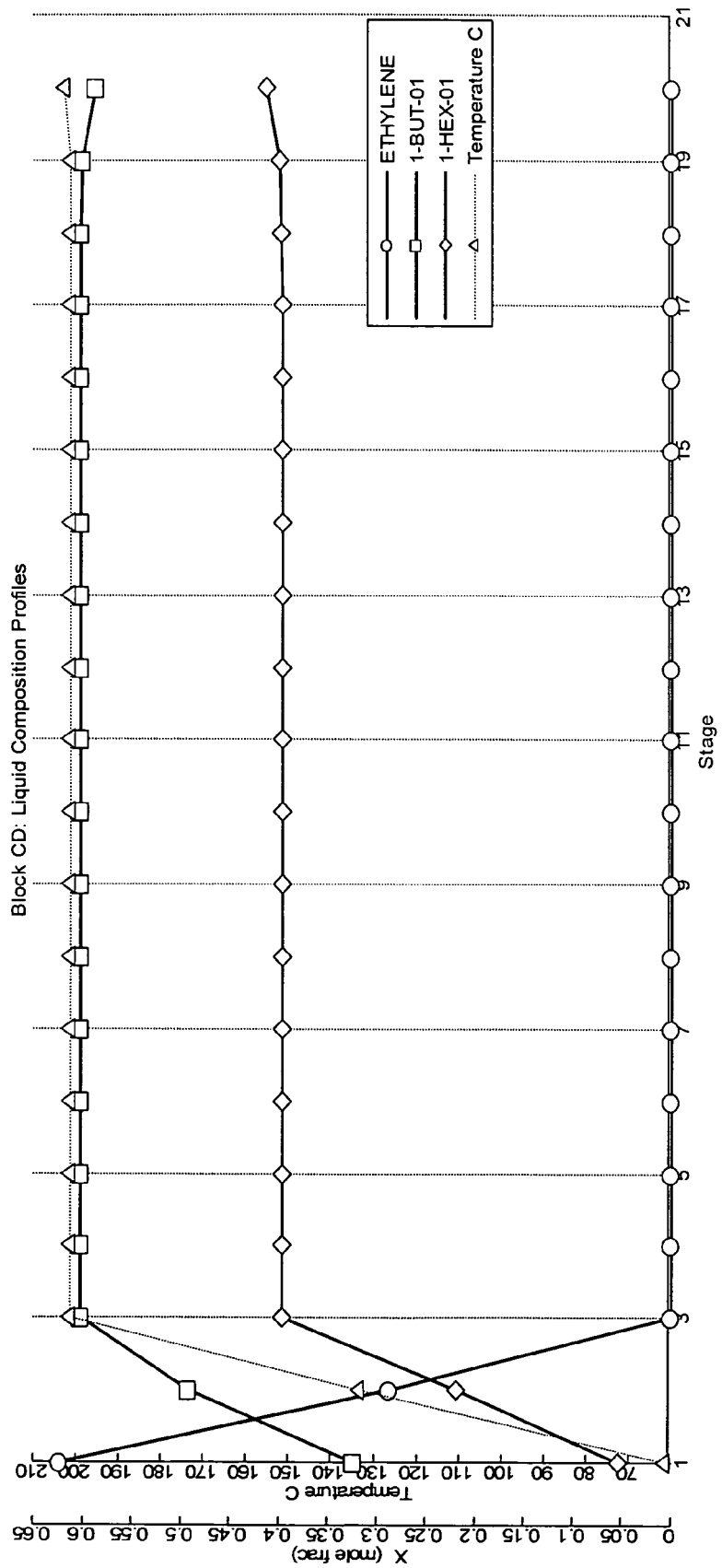
FIG. 6 shows a fifth profile of composition and temperature from modeling of the process of ethylene oligomerization using a catalytic distillation column. P=40 atm, RR=79, D/F=0.05, RXN=Stage 3, Equilibrium conversion=0.50, Total conversion of Ethylene=96.88%.

Referring to FIG. 1, an apparatus 10 having a catalytic distillation column 12 is provided for the present process. Column 12 has an upper first portion 14, a middle second portion 16 and a lower third portion 18. A condenser 20 is provided at first portion 14 for condensation of condensable components of a gas phase reaction mixture 27 for their return as liquids to first portion 14 of column 12. A reboiler 22 is provided at third portion 18 of column 12 for vaporization of the more volatile components of a liquid reaction mixture 28 there collected for return as volatiles to third portion 18 of column 12.

Second portion 16 of column 12 includes a catalyst bed 24 having therein an oligomerization catalyst 26. It has been found through experimental testing that preferably catalyst 26 is an acidic catalyst. The catalyst is considered to be acidic if it consumes a significant amount of base during titration. For example, the sulfated nickel/alumina(ALON) will consume $NH_3$ during a titration experiment. This finding is in agreement with that for a different system by Espinoza et al. in "Catalytic Oligomerization of Ethylene over Nickel-exchanged Amorphous Silica-alumina: Effect of the Acid Strength of the Support" *Appl. Catal.* 29, 295 (1987).

One preferred catalyst 26 comprises nickel (Ni) well-dispersed and supported on a non-porous alumina support, for example the commercial product ALON. We have found that such a catalyst has highly active Ni sites that enable the oligomerization process to be conducted under very mild conditions (about −10° C. to about 8° C.) for oligomerization of substantially pure ethylene(see below) as feed 30 when operated at, for example, about 40 to 50 atmospheres pressure. The desirable surface acidity is achieved via surface sulphation. Since ALON has only external surfaces and the reaction products are large molecules, the desorption of reaction products is enhanced(less products adsorbed on catalyst surface) resulting in higher reaction rate and improved catalyst stability.

In a second embodiment of apparatus 10 (not illustrated), there a plurality of catalyst beds 24 at different heights within column 12. When there are more than one catalyst beds 24, the temperature gradient within column 12 is smoothed out, and the relative concentration of feed (e.g. ethylene) 30 within column 12 is more readily controllable.

No added solvent is required in the reaction mixture.

It has been found that the oligomerization reactions of the present process (Equation 1 above) take place within catalyst bed 24. When the temperature and pressure are sufficiently high that ethylene 30 is present primarily as liquid (the critical temperature—boiling point—for ethylene is −8.9° C.), and the acidic catalyst 26 comprises Ni supported on non-porous alumina, contact between products 36 and ethylene 30 facilitates desorption of said products 36. The liquid ethylene 30 dissolves higher olefins 36 adsorbed on the catalyst surface active sites, so minimizing further catalytic reactions. Consequently there is minimization of olefin isomer or other by-product formation, thus enhancing selectivity to desirable terminal linear olefins (alpha-olefins).

Feed 30 is more volatile than products 36. When the process is operated at a sufficiently high temperature and pressure, products 36 are present primarily in liquid phase 28. Preferably, feed 30 is fed as liquid, and it is present as gas and liquid in equilibrium within the refluxing reaction mixture.

We will now summarize the process using ethylene as an example of feed 30. The ethylene feed 30 may be selected from substantially pure ethylene, typically 99.9% ethylene with 0.1% ethane as used in polyethylene manufacture, or a mixture rich in ethylene, for example an unfractionated industrial ethylene stream comprising, typically, about 80.5% ethylene, 18.2% ethane and 1.3% acetylene. Optionally, the acetylene may be removed or converted before being fed to the oligomerization reactor. It will be appreciated by those skilled in the art that the reaction parameters to provide the low olefin feed in liquid form at its boiling point will vary somewhat for different compositions of the feed mixture rich in ethylene. For example, when feed 30 comprises the above unfractionated industrial ethylene stream, the mixture flashes between 16° C. and 17.5° C. at 50 atm. It will also be appreciated that when the low olefin feed composition includes C3, C4, C5 etc., the temperature and pressure required to provide the feed in the requisite liquid form, will be different ie different boiling points.

Liquid ethylene 30 is fed via an inlet line 32 to upper portion 14 of column at a position above an upper surface 34 of catalyst bed 24. Ethylene 30 is oligomerized to a series of higher olefins $CnH_2n$ 36 which mix with ethylene to form liquid phase reaction mixture 28 that descends via a bottom surface 38 of catalyst bed 24 to collect in third portion 18 of column 12. Liquid ethylene 30 supplied via line 32 washes liquid phase products 36 off the catalyst surface as liquid mixture 28. Thus ethylene 30 is continuously supplied, reacts within catalyst bed 24, and with products 36 descends as liquid mixture 28.

The position of inlet line 32 as shown in FIG. 1 is above catalyst bed 24. It will be recognized by those skilled in the art that inlet line 32 may be positioned above, below, or at some point within the vertical extent of catalyst bed 24. Further, there may be more than one feed line 32 positioned at different heights on column 12. The product distribution is affected by the positioning of inlet line 32. The distribution within the slate of products can be controllably varied by amending the position of inlet line 32, and controlling the reflux rate and the reboiler duty. It should be noted that line 42 is optional. It is required only if there present impurities in the gas phase at the condenser.

Liquid product mixture 28 is removed via reboiler 22, from which the more volatile components, and in particular ethylene, are returned as volatiles to column 12. The remaining portion is liquid products 36 that are removed via line 40.

The rate of feed of ethylene 30, the process operating conditions, and the rate of removal of liquid products determines the composition of the product liquid removed from column 12. Preferably, the reaction is operated at elevated pressure, for example 40 atmospheres, so as to maintain ethylene 30 at its boiling point. The process operates at low temperatures, preferably from about −20° C. to about 8° C., and more preferably at −10° C. to 8° C., when operated at 40 to 50 atmospheres pressure. Under these conditions ethylene is present primarily as liquid at its boiling point in first portion 14 of column 12, and as a solution with products 36 as a condensed phase 28 within catalyst bed 24 and in third portion 18 of column 12. It is desirable to run the CD column at the highest possible temperature where ethylene is a liquid at its boiling point (both gas and liquid are present). At the top of the column, there are no products and so it is preferable to operate at the boiling point of ethylene (about 8° C. at 50 atm) in this zone. The temperature of the bed increases once products are formed, or when higher boiling components such as ethane are present.

It is well known that industrial ethylene contains impurities, including ethane. Further, ethane or other light hydrocarbons may accumulate in the reaction mixture and, as they are volatile, primarily in first portion 14 of column 12. Thus it will be necessary to remove these volatile materials 44, from time to time when operating in batch mode or continuously when operating a continuous process. A stream containing the undesirable volatiles 44 is removed via outlet line 42.

The new process for oligomerization of olefins, and in particular oligomerization of ethylene, has the following beneficial characteristics. Several catalysts are active for oligomerization of ethylene, including homogeneous catalysts and heterogeneous catalysts. One preferred catalyst has highly active Ni sites that enable oligomerization process at very mild conditions. The desirable surface acidity is achieved via surface sulphation. This preferred catalyst comprises Ni well dispersed and supported on a non-porous alumina support, thus facilitating product desorption, consequently minimizing isomer formation, and so enhancing selectivity to desirable terminal linear olefins (alpha-olefins). Both liquid feed and higher olefins formed through oligomerization of the feed also serve as the liquid medium, without added solvent, thus facilitating product desorption from the catalyst surface.

Use of catalytic distillation column 12 provides further advantages. The heat of exothermic reaction (22 kcal/mol) is used to reduce energy requirement in the distillation step. There are no hot spots, and so there is no need for an intercooler. Solvent is not required as the liquid feed and product higher olefins 36 serve as solvent, and only feed olefin is fed to the column. The resulting high reactant concentration results in low mass transfer resistance and high reaction rate. The acidic $Ni/Al_2O_3$ catalyst, details of which are described in Example 1 below, has superior selectivity and stability. At least one fixed catalyst bed 24 is used as the reactor in catalytic distillation column 12, and there is no need to provide another column for separation of catalyst from the reaction mixtures, in contrast to possible highly acidic homogeneous reactive distillation systems that may be used without solvent. Thus, while the heterogeneous reaction is substantially similar to the liquid phase reaction used in several present commercial processes, the catalyst and catalytic distillation process described herein confer significant additional benefits.

EXAMPLES

Example 1

Activity of Catalyst Comprising Ni Supported on Alumina

We have shown that the data reported by Zhang et al. in "Oligomerization of Ethylene in a Slurry Reactor Using a Nickel/Sulfated Alumina Catalyst" *Ind. Eng. Chem. Res.* 36, 3433-3438 (1997) are reproducible, and that the catalyst is useful for the present invention under catalytic distillation conditions.

Zhang et al. conducted a series of experimental runs using a batch reactor and under mild operating conditions when using heptane as solvent. The catalyst Ni/ALON, prepared as described by them, was shown to be highly active when used under the following operating conditions:

Reaction temperatures: 278, 298, 308, 323 K
Pressure: 170.26 kPa.
Run duration in a Parr reactor: 3 h
n-Heptane (solvent) charge: 120 mL
Stirring speed: 450 rpm
Catalyst: 1.7 wt % Ni and 5.0 wt % $SO_4^{2-}$
Catalyst charge: 0.2, 0.3, 0.4, 0.5 g The catalyst is highly active for oligomerization. It was found that the process has first order kinetics with respect to ethylene (Eq. 2) and the activation energy is 16.3 kJ/mol. Neither inter-nor intra-particle resistances may be ignored with this catalyst. The combined resistance to external diffusion, internal diffusion and reaction, expressed as in Eq. 3, is the controlling step.

$$\frac{C_i}{R_a} = \frac{1}{k_b a_b} + \frac{1}{m}\left(\frac{1}{k_c a_c} + \frac{1}{k\eta}\right) \quad \text{i. (2)}$$

$$R_{cr} = \frac{1}{k_c a_c} + \frac{1}{k\eta} \quad \text{ii. (3)}$$

At low temperatures (<298 K) and near-atmospheric pressure, high selectivities to 1-butene and 1-hexene can be attained when using n-heptane as solvent. No apparent deactivation occurs under these conditions.

Example 2

Simulation of the Process with Different Operating Parameters

Figure 7:
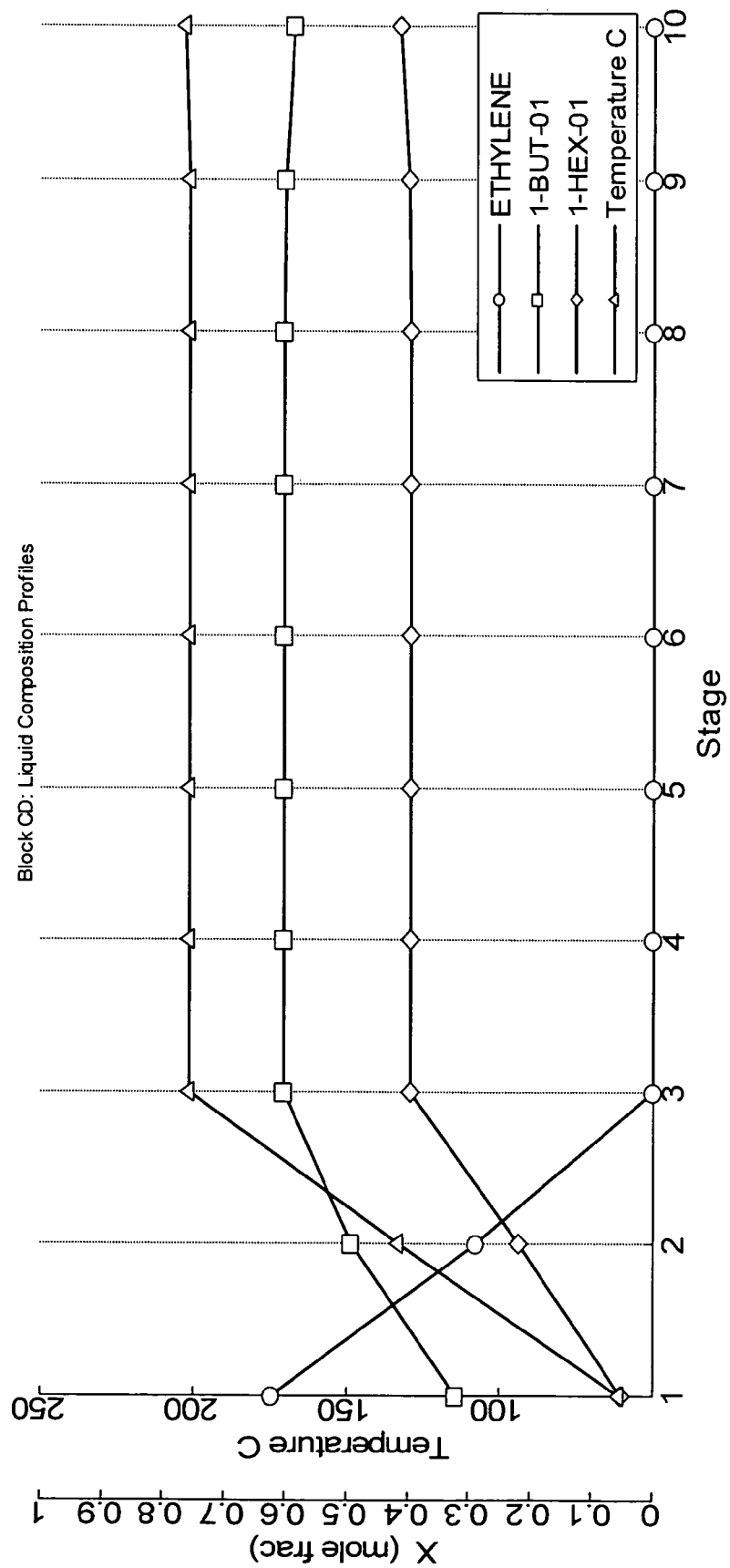
FIG. 7 shows a sixth profile of composition and temperature from modeling of the process of ethylene oligomerization using a catalytic distillation column. P=40 atm, RR=79, D/F=0.05, RXN=Stage 3, Equilibrium conversion=0.50, Total conversion of Ethylene=96.88%

The following are data obtained through simulations using ASPEN PLUS® software. The design was based on a column equipped with 20 equilibrium stages. The simulation results show the temperature and concentration profiles along the column. At the top of the column (stage 1), it can be seen from the concentration profile that its composition is similar to the feed (mostly C2=). At the bottom of the column (stage 20), the product contains C4= and C6= and residual C2=. In the simulation it is assumed that the oligomerization produces only C4= and C6= to a different fraction of equilibrium concentrations. The results on product distribution are shown in FIGS. 2-6. FIG. 7 is another simulation run with only 10 equilibrium stages in the column, all other conditions are identical to those used in FIG. 6. The temperature profile provides the design data for choosing the reboiler and the condenser.

It will be appreciated by those skilled in the art that various forms of device can be used for presentation of catalysts within at least one catalyst bed of a catalytic distillation column.

FIGS. 2 through 7 show the concentration and temperature profiles throughout column 12 using different sets of process operating parameters for oligomerization of ethylene to higher olefins. In each case, the reactions occurred over catalyst 26 within catalyst bed 24.

Under each set of conditions, reaction occurs sufficiently rapidly that there is little ethylene present in third portion 18 of column, and ethylene dissolved in liquid phase 28 is returned to column 12 as volatiles from reboiler 22. The small proportion of olefin products 36 present in the vapor phase at first portion 14 of column 12 are returned as liquid from condenser 20.

It should be noted that the catalytic distillation column can be operated with a homogeneous catalyst. In this case the catalyst is mixed with feed ethylene and introduced at the top of the column.

REFERENCES CITED

U.S. Patent Documents
U.S. Pat. No. 6,841,711 Krug et al. Process for making a lube base stock from a lower molecular weight feedstock in a catalytic distillation unit
U.S. Pat. No. 6,274,783 Gildert et al. Catalytic distillation process for the production of C8 alkanes
U.S. Pat. No. 6,025,533 Vora et al. Oligomer production with catalytic distillation
U.S. Pat. No. 6,004,256 Townsend et al. Catalytic distillation oligomerization of vinyl monomers to mke polymerizable vinyl monomer oligomers, uses thereof and methods for same U.S. Patent Applications
2007/0123743A1 Ng et al. Composite catalyst for the selective oligomerization of lower alkenes and the production of high octane products Foreign Patent Documents
French Patent 2641 477 C. Yves and C. Dominique "Process for the preparation and use, in the dimerisation of olefins, of a catalyst containing nickel, sulphur and alumina Other References
Q. Zhang, M. Kantcheva, I. G. Dalla Lana, "Oligomerization of Ethylene in a Slurry Reactor Using a Nickel/Sulfated Alumina Catalyst" *Ind. Eng. Chem. Res.* 36, 3433-3438 (1997).
R. L. Espinoza, R. Snel, C. J. Corf, C. P. Nicolaide, "Catalytic Oligomerization of Ethylene over Nickel-exchanged Amorphous Silica-alumina: Effect of the Acid Strength of the Support" *Appl. Catal.* 29, 295 (1987).

The invention claimed is:

1. A process for making linear higher olefins of a general formula $C_nH_{2n}$, wherein n is an integer greater than two, comprising:
    (a) providing an apparatus including a catalytic distillation column comprising an upper first portion, a condenser connected to the upper first portion, a middle second portion having a catalyst bed containing an oligomerization catalyst having a good selectivity to formation of linear higher olefins a lower third portion, and a reboiler connected to the lower third portion of the column,
    (b) providing a feed composition comprising a lower olefin having a general formula $C_nH_{2n}$ wherein n is an integer from 2-5,
    (c) introducing the feed composition in liquid form at its boiling point into the upper first portion,
    (d) passing the feed composition from the upper first portion to the middle second portion, wherein the temperature and pressure are sufficiently high that the feed composition is present as gas and liquid in equilibrium within a refluxing reaction mixture, such that the lower olefin is oligornerized by reacting the lower olefin over the oligomerization catalyst so as to form a liquid reaction mixture containing higher olefins which mixes with the lower olefin to form a liquid phase product solution that descends to collect in the lower third portion and a gas phase reaction mixture that ascends to the upper first portion,
    (e) passing the gas phase reaction mixture from the upper first portion to the condenser for condensation of the condensable components for their return as liquids to the upper first portion, and
    (f) passing the liquid phase product solution to the reboiler, wherein the lower olefin is separated and returned as vapor to the lower third portion and the linear higher olefins are recovered as liquid.

2. A process according to claim 1, wherein the feed composition comprises 99.9% of ethylene and 0.1% of ethane.

3. A process according to claim 1, wherein the feed composition comprises 80.5% of ethylene, 18.2% of ethane and 1.3% of acetylene, and
    wherein the temperature is 16-17.5° C. and the pressure is 50 atmospheres.

4. A process according to claim 1, wherein the lower olefin is ethylene and the higher olefins are oligomers of ethylene.

5. A process according to claim 4, wherein the catalyst comprises an acidic heterogeneous catalyst.

6. A process according to claim 4, wherein the catalyst is nickel supported on sulfonated non-porous alumina.

7. A process according to claim 6, wherein the temperature is about −20° C. to about 8° C. and the pressure is 40 to 50 atmospheres.

8. A process according to claim 1, wherein the catalyst is a homogeneous catalyst.

9. A process according to claim 1, wherein the catalyst is a Ziegler type nickel complex.

10. A process according to claim 1, wherein the process is continuous.

* * * * *